United States Patent
Govari et al.

(10) Patent No.: US 11,547,476 B2
(45) Date of Patent: *Jan. 10, 2023

(54) ESTIMATING A TEMPERATURE DURING ABLATION

(71) Applicant: BIOSENSE WEBSTER (ISRAEL) LTD., Yokneam (IL)

(72) Inventors: Assaf Govari, Haifa (IL); Yaron Ephrath, Karkur (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 699 days.

This patent is subject to a terminal disclaimer.

(21) Appl. No.: 16/561,354

(22) Filed: Sep. 5, 2019

(65) Prior Publication Data

US 2019/0388146 A1 Dec. 26, 2019

Related U.S. Application Data

(60) Continuation of application No. 16/269,851, filed on Feb. 7, 2019, which is a division of application No. (Continued)

(51) Int. Cl.
*A61B 18/12* (2006.01)
*A61B 18/14* (2006.01)
*A61B 18/00* (2006.01)

(52) U.S. Cl.
CPC ...... *A61B 18/1492* (2013.01); *A61B 18/1206* (2013.01); *A61B 2018/00011* (2013.01); (Continued)

(58) Field of Classification Search
CPC ...... A61B 18/1492; A61B 2018/00029; A61B 2018/00351; A61B 2018/00577; (Continued)

(56) References Cited

U.S. PATENT DOCUMENTS 5,688,267 A  11/1997  Panescu
5,702,386 A  12/1997  Stern et al.
(Continued)

FOREIGN PATENT DOCUMENTS

EP  2875791 A1  5/2015
EP  3338723 B1  9/2019
(Continued)

OTHER PUBLICATIONS

Search Report from corresponding Japanese Patent Application No. 2017242500A, dated Aug. 20, 2021.
(Continued)

*Primary Examiner* — Daniel W Fowler
(74) *Attorney, Agent, or Firm* — Dergosits & Noah LLP; Todd A. Noah

(57) ABSTRACT

A method for use with an intra-body probe, a distal end of which includes an ablation electrode and a temperature sensor, is described. While (i) the ablation electrode is driving an ablating current into tissue of a subject, and (ii) fluid is passed from the distal end of the intra-body probe at a fluid-flow rate, a processor receives a temperature sensed by the temperature sensor. The processor estimates a temperature of the tissue, based at least on the sensed temperature and at least one parameter selected from the group consisting of: the fluid-flow rate, and a parameter of the ablating current. The processor generates an output in response to the estimated temperature. Other embodiments are also described.

13 Claims, 4 Drawing Sheets

Related U.S. Application Data

14/998,204, filed on Dec. 24, 2015, now Pat. No. 10,213,253.

(52) U.S. Cl.
CPC .............. *A61B 2018/00029* (2013.01); *A61B 2018/00351* (2013.01); *A61B 2018/00577* (2013.01); *A61B 2018/00648* (2013.01); *A61B 2018/00696* (2013.01); *A61B 2018/00702* (2013.01); *A61B 2018/00708* (2013.01); *A61B 2018/00744* (2013.01); *A61B 2018/00791* (2013.01); *A61B 2018/00797* (2013.01); *A61B 2018/00827* (2013.01); *A61B 2018/00863* (2013.01); *A61B 2018/00898* (2013.01); *A61B 2018/00988* (2013.01); *A61B 2218/002* (2013.01)

(58) Field of Classification Search
CPC .......... A61B 2018/00696; A61B 2018/00702; A61B 2018/00791; A61B 2018/008727; A61B 2018/00863; A61B 2018/00898; A61B 2018/00988
See application file for complete search history.

(56) References Cited

U.S. PATENT DOCUMENTS

| | | |
|---|---|---|
| 5,957,961 A | 9/1999 | Maguire et al. |
| 6,022,346 A | 2/2000 | Panescu et al. |
| 6,122,551 A | 9/2000 | Rudie |
| 6,197,023 B1 | 3/2001 | Muntermann |
| 6,217,574 B1 | 4/2001 | Webster |
| 6,312,425 B1 | 11/2001 | Simpson et al. |
| 6,391,024 B1 | 5/2002 | Sun et al. |
| 6,730,077 B2 | 5/2004 | Carroll et al. |
| 2001/0032002 A1 | 10/2001 | McClurken |
| 2004/0078036 A1 | 4/2004 | Keidar |
| 2008/0058705 A1 | 3/2008 | Wiksell |
| 2008/0262578 A1 | 10/2008 | Langberg |
| 2009/0270954 A1 | 10/2009 | Schenck |
| 2009/0312754 A1 | 12/2009 | Lenihan |
| 2010/0030209 A1 | 2/2010 | Govari et al. |
| 2010/0204560 A1 | 8/2010 | Salahieh |
| 2011/0118727 A1* | 5/2011 | Fish .................. A61B 5/01 606/34 |
| 2011/0208180 A1* | 8/2011 | Brannan ............ A61B 18/1815 606/33 |
| 2013/0060243 A1 | 3/2013 | Kuhn |
| 2014/0171936 A1 | 6/2014 | Govari et al. |
| 2014/0276562 A1 | 9/2014 | Govari et al. |
| 2015/0105765 A1 | 4/2015 | Panescu et al. |
| 2015/0164570 A1 | 6/2015 | Wittenberger et al. |
| 2016/0106492 A1 | 4/2016 | Honda et al. |
| 2016/0278856 A1 | 9/2016 | Panescu et al. |

FOREIGN PATENT DOCUMENTS

| | | |
|---|---|---|
| JP | H11506947 A | 6/1999 |
| JP | 2007222687 A | 9/2007 |
| JP | 05102270 B2 | 12/2012 |
| JP | 2014176693 A | 9/2014 |
| WO | 1996000043 | 1/1996 |
| WO | 1996036860 | 11/1996 |
| WO | WO2007/005963 A2 | 1/2007 |

OTHER PUBLICATIONS

Office Action from corresponding Chinese Patent Application No. 201711376778.2, dated Jul. 21, 2020.

* cited by examiner

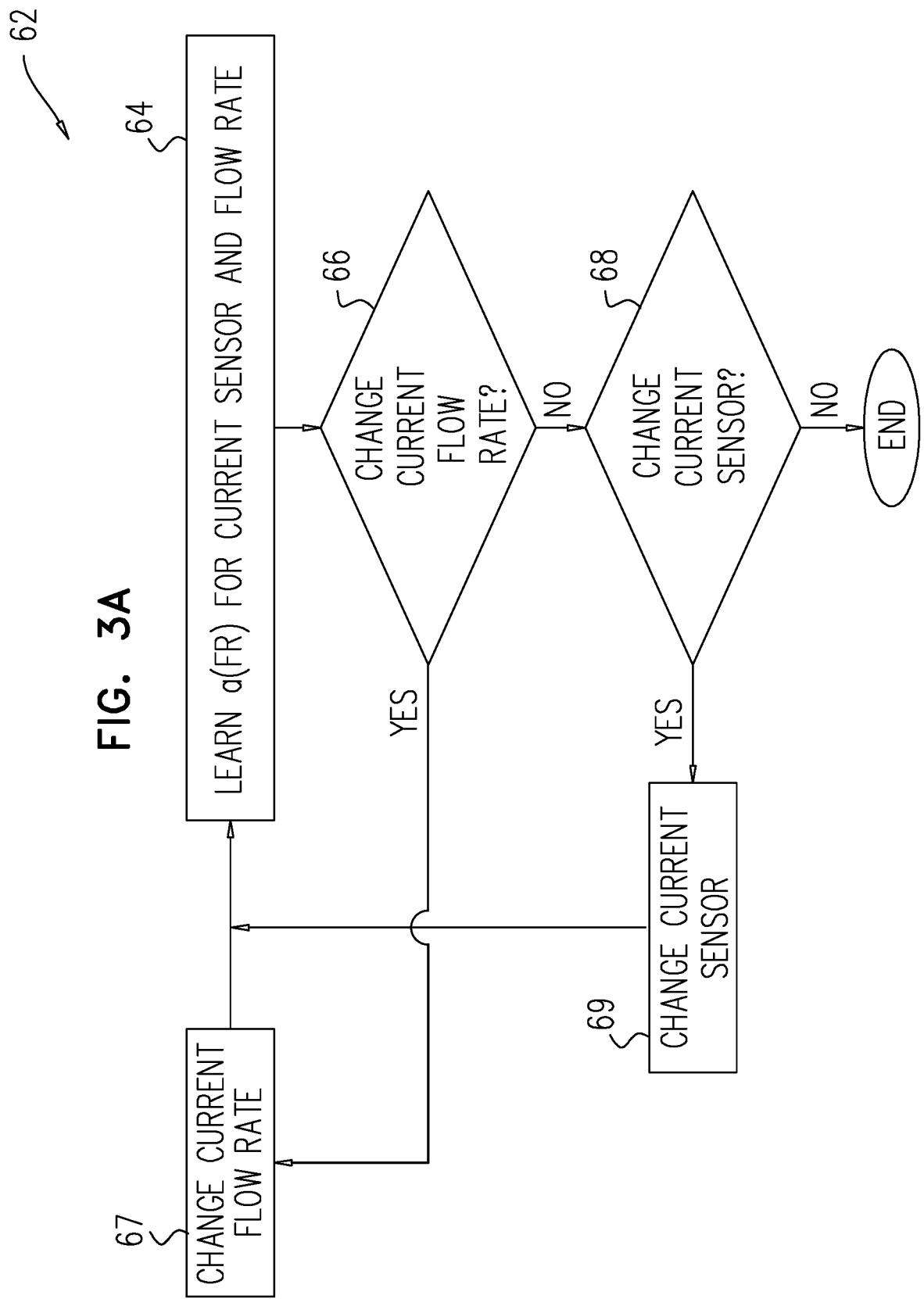

ESTIMATING A TEMPERATURE DURING ABLATION

CROSS REFERENCE TO RELATED APPLICATION

This patent application is a continuation of U.S. patent application Ser. No. 16/269,851 filed on Feb. 7, 2019 which is a divisional of U.S. patent application Ser. No. 14/998,204 filed on Dec. 24, 2015, now U.S. Pat. No. 10,213,253.

FIELD OF THE INVENTION

The present invention relates generally to invasive medical devices, and particularly to probes used in ablating tissue within the body.

BACKGROUND

Minimally-invasive intracardiac ablation is the treatment of choice for various types of arrhythmias. To perform such treatment, the physician typically inserts a catheter through the vascular system into the heart, brings the distal end of the catheter into contact with myocardial tissue in areas of abnormal electrical activity, and then energizes one or more electrodes at or near the distal end in order to create tissue necrosis.

U.S. Patent Application Publication 2010/0030209, whose disclosure is incorporated herein by reference, describes a catheter with a perforated tip, which includes an insertion tube, having a distal end for insertion into a body of a subject. A distal tip is fixed to the distal end of the insertion tube and is coupled to apply energy to tissue inside the body. The distal tip has an outer surface with a plurality of perforations through the outer surface, which are distributed circumferentially and longitudinally over the distal tip. A lumen passes through the insertion tube and is coupled to deliver a fluid to the tissue via the perforations.

U.S. Pat. No. 5,957,961, whose disclosure is incorporated herein by reference, describes a catheter having a distal segment carrying at least one electrode extending along the segment and having a number of temperature sensors arranged along the distal segment adjacent the electrode, each providing an output indicative of temperature. The catheter is coupled to a power source, which provides RF energy to the electrode. Temperature processing circuitry is coupled to the temperature sensors and the power source, and controls power output from the power source as a function of the outputs of the temperature sensors.

U.S. Pat. No. 6,312,425, whose disclosure is incorporated herein by reference, describes an RF ablation catheter tip electrode with multiple thermal sensors. A tip thermal sensor is located at or near the apex of the distal-end region, and one or more side thermal sensors are located near the surface of the proximal-end region. The electrode is preferably an assembly formed from a hollow dome-shaped shell with a core disposed within the shell. The side thermal sensor wires are electrically connected inside the shell and the core has a longitudinal channel for the side thermal sensor wires welded to the shell. The shell also preferably has a pocket in the apex of the shell, and the end thermal sensor wires pass through the core to the apex of the shell.

U.S. Pat. No. 6,217,574, whose disclosure is incorporated herein by reference, describes an irrigated split tip electrode catheter. A signal processor activates an RF generator to transmit a low level RF current to each electrode member of the split tip electrode. The signal processor receives signals indicative of the impedance between each electrode member and one or more surface indifferent electrodes and determines which electrode members are associated with the highest impedance. Such electrode members are stated to be those in greatest contact with the myocardium.

U.S. Pat. No. 6,391,024, whose disclosure is incorporated herein by reference, describes a method of assessing the adequacy of contact between an ablation electrode and biological tissue. The method measures the impedance between an ablation electrode and a reference electrode at a first and second frequencies. A percentage difference between the first-frequency impedance and the second-frequency impedance is stated to provide an indication of the state of electrode/tissue contact.

U.S. Pat. No. 6,730,077, whose disclosure is incorporated herein by reference, describes a cryocatheter for treatment of tissue. A signal conductor extends through the catheter to the catheter tip and connects to a thermally and electrically conductive shell or cap that applies an RF current to the region of tissue contacted by the tip. A tissue impedance path between the signal lead and a surface electrode mounted on the patient's skin is monitored to develop a quantitative measure of tissue contact at the distal tip.

U.S. Patent Application Publication 2014/0171936 to Govari, which is incorporated herein by reference, describes apparatus that includes an insertion tube having a distal end configured for insertion into proximity with tissue in a body of a patient and containing a lumen having an electrical conductor for conveying electrical energy to the tissue. The apparatus further includes a conductive cap attached to the distal end of the insertion tube and coupled electrically to the electrical conductor, wherein the conductive cap has an outer surface. In addition there are a multiplicity of optical fibers contained within the insertion tube, each fiber terminating in proximity to the outer surface of the cap, and being configured to convey optical radiation to and from the tissue while the electrical energy is being conveyed to the tissue.

SUMMARY OF THE INVENTION

There is provided, in accordance with some embodiments of the present invention, a method for use with an intra-body probe, a distal end of which includes an ablation electrode and a temperature sensor. While (i) the ablation electrode is driving an ablating current into tissue of a subject, and (ii) fluid is passed from the distal end of the intra-body probe at a fluid-flow rate, a processor receives a temperature sensed by the temperature sensor. The processor estimates a temperature of the tissue, based at least (i) on the sensed temperature and (ii) the fluid-flow rate and/or a parameter of the ablating current. The processor generates an output in response to the estimated temperature.

In some embodiments, the at least one parameter includes a power of the ablating current.

In some embodiments, estimating the temperature of the tissue includes estimating the temperature of the tissue at an interface of the tissue and the electrode.

In some embodiments, the temperature is sensed while the temperature sensor is not in contact with the tissue.

In some embodiments, the method further includes adjusting a power of the ablating current in response to the output.

In some embodiments, adjusting the power of the ablating current includes stopping the ablating current.

In some embodiments, the method further includes changing the fluid-flow rate, in response to the output.

In some embodiments, the method further includes, in response to the output, changing a force with which the electrode is pressed against the tissue.

In some embodiments, estimating the temperature of the tissue includes:

selecting a coefficient in response to the at least one parameter; and estimating the temperature of the tissue, at least by multiplying, by the coefficient, a value that is based on the sensed temperature.

In some embodiments, selecting the coefficient includes computing the coefficient by interpolation.

There is further provided, in accordance with some embodiments of the present invention, apparatus for use with an intra-body probe, a distal end of which includes an ablation electrode and a temperature sensor. The apparatus includes an interface configured to connect to the intra-body probe, and a processor. While (i) the ablation electrode is driving an ablating current into tissue of a subject, and (ii) fluid is passed from the distal end of the intra-body probe at a fluid-flow rate, the processor receives from the temperature sensor, via the interface, a temperature sensed by the temperature sensor. The processor estimates a temperature of the tissue, based at least on (i) the sensed temperature, and (ii) the fluid-flow rate and/or a parameter of the ablating current. The processor generates an output in response to the estimated temperature.

There is further provided, in accordance with some embodiments of the present invention, a method for use with a probe that includes an ablation electrode and a temperature sensor. The method includes performing a plurality of ablations of tissue, using the ablation electrode. During each of the ablations, (i) fluid is passed from the probe at a fluid-flow rate, (ii) a temperature is sensed, using the temperature sensor, and (iii) a temperature of the tissue is measured. From the ablations, a relationship between the sensed temperatures and the measured temperatures is learned.

In some embodiments, learning the relationship includes learning the relationship by regressing a variable that is based on the measured temperatures on a variable that is based on the sensed temperatures.

In some embodiments, the regressing includes performing a linear regression.

In some embodiments, performing the plurality of ablations includes performing at least two ablations whose ablation powers differ from each other.

In some embodiments, performing the plurality of ablations includes performing at least two ablations that differ from each other in a force with which the electrode is pressed against the tissue.

The present invention will be more fully understood from the following detailed description of embodiments thereof, taken together with the drawings, in which:

BRIEF DESCRIPTION OF THE DRAWINGS

FIG. 3A is a flow diagram for a method for learning a coefficient, in accordance with some embodiments of the present invention.

DETAILED DESCRIPTION OF EMBODIMENTS

Overview

It has been found that cooling (or "irrigating") the area of the ablation site reduces thrombus (blood clot) formation. For this purpose, for example, Biosense Webster Inc. (Diamond Bar, Calif.) offers the ThermoCool® irrigated-tip catheter for use with its CARTO® integrated mapping and ablation system. The metal catheter tip, which is energized with radio-frequency (RF) electrical current to ablate the tissue, has a number of peripheral holes, distributed circumferentially around the tip, for irrigation of the treatment site. During the procedure, a pump coupled to the catheter delivers an irrigating saline solution to the catheter tip, and the solution flows out through the holes. (In some embodiments, even while no ablating current is being passed into the tissue, the flow of irrigating fluid is maintained, e.g., at a reduced flow rate.)

When performing an ablation procedure, it is often advantageous to position one or more temperature sensors near the tissue that is being ablated, to help provide feedback to the operating physician. For example, if the temperature sensors sense that the tissue is being overheated, the operating physician may stop the ablation procedure or modify ablation parameters.

At least in some cases, to measure the temperature at the tissue-electrode interface as accurately as possible, the temperature sensors would ideally be positioned such that they contact the tissue. However, due to regulatory concerns, and/or for other reasons, contacting the tissue with the temperature sensors may not be feasible. Hence, a particular challenge, when sensing the temperature of the tissue, is that a sensor that is not in contact with the tissue may sense a temperature that is lower than the actual temperature of the tissue at the tissue-electrode interface. Furthermore, regardless of whether the sensors are in contact with the tissue, the flow of irrigating fluid (e.g., saline) from the ablation electrode may cause the sensors to sense a temperature that is lower than that which the sensors would have otherwise sensed. For example, the irrigating fluid may function as a heat sink, transferring heat away from the temperature sensors.

Embodiments of the present invention address these challenges, by providing methods and apparatus for estimating a temperature of the tissue, at least at the tissue-electrode interface, based at least on the sensed temperature and the flow rate of the irrigating fluid.

System Description

Figure 1:
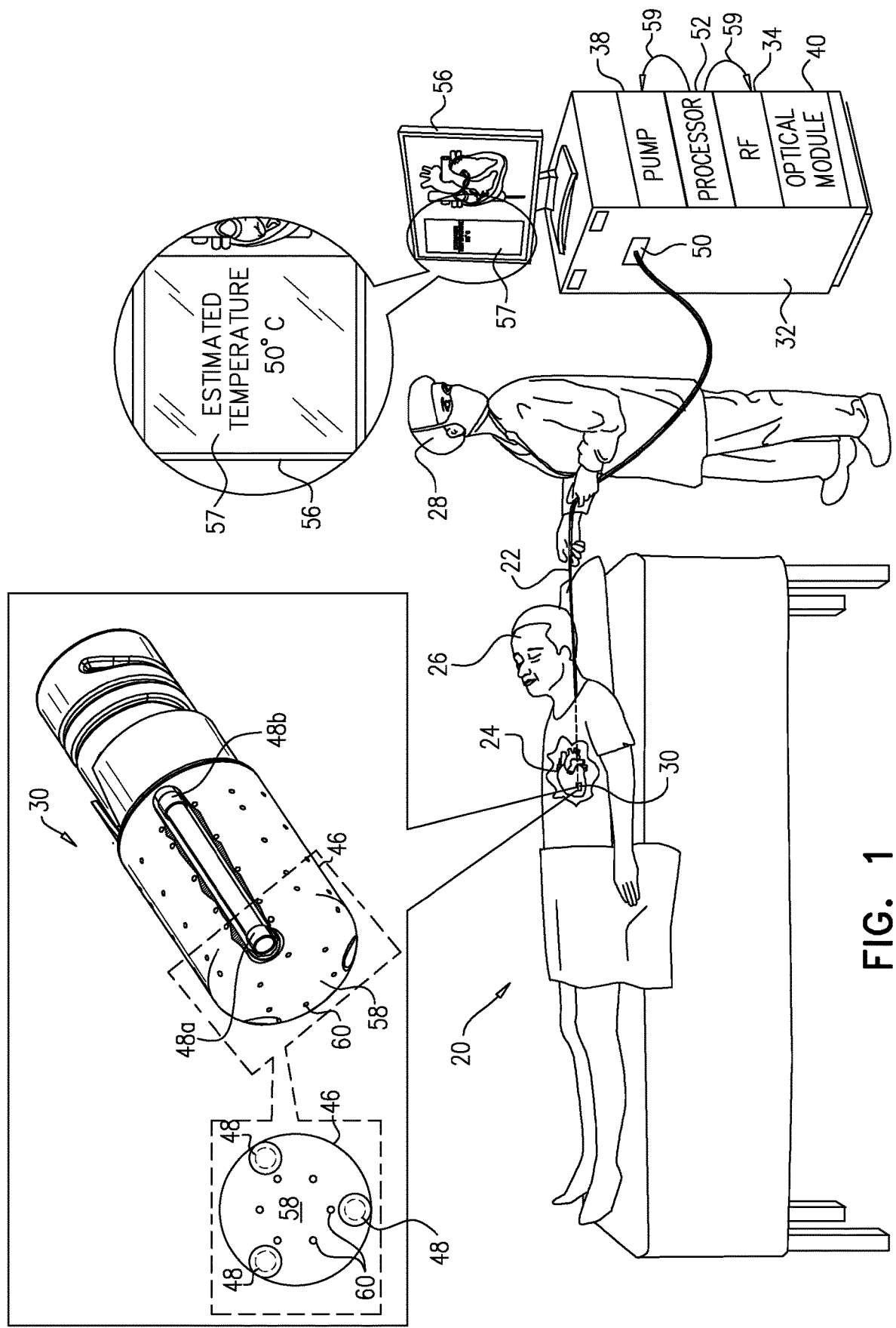
FIG. 1 is a schematic pictorial illustration of a system for cardiac ablation treatment, in accordance with some embodiments of the present invention.

Reference is initially made to FIG. 1, which is a schematic pictorial illustration of a system 20 for cardiac ablation treatment, in accordance with an embodiment of the present invention. An operator 28 (such as an interventional cardiologist) inserts an intra-body probe, such as a catheter 22, via the vascular system of a patient 26, into a chamber of the patient's heart 24. For example, to treat atrial fibrillation, the operator may advance the catheter into the left atrium and bring a distal end 30 of the catheter into contact with myocardial tissue that is to be monitored and/or ablated.

Catheter 22 is connected at its proximal end to a console 32. Console 32 comprises an RF energy generator 34, which supplies electrical power via catheter 22 to distal end 30 in order to ablate the target tissue. A processor 52 tracks the temperature of the tissue at distal end 30 by processing the outputs of temperature sensors in the distal end, as described below. An irrigation pump 38 supplies an irrigating fluid, such as saline solution, through catheter 22 to distal end 30. In addition, in some embodiments, an optical module 40 provides optical radiation, typically from, but not limited to, a laser, an incandescent lamp, an arc lamp, or a light emitting diode (LED), for transmission from distal end 30 to the target tissue. The module receives and analyzes optical radiation returning from the target tissue and acquired at the distal end.

On the basis of information provided by the temperature sensors and/or optical module 40, processor 52 may control the power applied by RF energy generator 34 and/or the flow of fluid provided by pump 38, either automatically or in response to inputs from operator 28, as further described hereinbelow.

System 20 may be based on the above-mentioned CARTO system, for example, which provides extensive facilities to support navigation and control of catheter 22.

Distal end 30 of catheter 22 includes an ablation electrode 46, which includes a distal face 58. Typically, when performing the ablation, a portion of ablation electrode 46 (e.g., distal face 58) is brought into contact with (e.g., pressed against) the tissue that is to be ablated, and subsequently, radiofrequency energy, supplied by RF energy generator 34, is applied to the tissue by the ablation electrode. As shown in FIG. 1, ablation electrode 46 may be shaped to define a plurality of perforations 60. During the procedure, irrigating fluid, supplied by irrigation pump 38, is passed from perforations 60. The passing of the irrigating fluid may help prevent blood clots from forming, by cooling and diluting the blood in the vicinity of the ablation site.

As shown in the figure, a plurality of temperature sensors 48 (e.g., thermocouples) are disposed at various respective positions on and/or within ablation electrode 46. In particular, the "head-on" view of distal face 58 shows three circumferentially-arranged temperature sensors 48 near the distal face 58 of the electrode, each of the temperature sensors being contained within a lumen in the wall of the electrode. The isometric view of distal end 30, which "cuts away" the outer wall of one of the lumens, shows two temperature sensors within the lumen—(i) a distal temperature sensor 48a, which is one of the three sensors shown in the distal-end view, and (ii) a proximal temperature sensor 48b, which is one of three proximal sensors that are not shown in the distal-end view. Distal end 30, as shown in FIG. 1, thus comprises a total of six temperature sensors. (Notwithstanding the above, it is noted that the scope of the present disclosure includes the use of any suitable number and arrangement of temperature sensors.)

While the ablation electrode is used to drive an ablating current into the tissue, and while the irrigating fluid is passed from the distal end of the catheter (e.g., through perforations 60), one or more of the temperature sensors are used to sense respective temperatures.

In general, it is advantageous to have a plurality of temperature sensors disposed at various locations with respect to the tissue, e.g., in that information regarding the orientation of the ablation electrode may be deduced from the various temperature readings provided by the sensors. For example, if each of the three distal sensors senses approximately the same temperature (indicating that the three distal sensors are approximately equidistant from the tissue), and/or if each of the three proximal sensors senses approximately the same temperature (indicating that the three proximal sensors are approximately equidistant from the tissue), it may be deduced that the electrode is oriented perpendicularly with respect to tissue, as is typically desired. Conversely, if, for example, one of the proximal sensors senses a temperature that is higher than that sensed by the other two proximal sensors, it may be deduced that the ablation electrode is not oriented perpendicularly with respect to the tissue, such that one of the proximal sensors is closer to the tissue than the other proximal sensors.

Aside from providing information concerning the orientation of the catheter, the temperature sensors may facilitate the performance of the ablation, by indicating whether the tissue at the tissue-electrode interface is at the desired temperature for ablation. However, as noted above, a temperature sensor that is not in contact with the tissue may sense a temperature that is lower than the actual temperature of the tissue at the tissue-electrode interface. For example, distal sensor 48a may be disposed somewhat proximally to distal face 58, such that distal sensor 48a is generally not in contact with the tissue during the ablation procedure. Consequently, the temperature sensed by distal sensor 48a is typically lower than the actual temperature of the tissue at the interface. The difference between the actual temperature and the sensed temperature is typically even greater for proximal sensor 48b, which is farther from the tissue than distal sensor 48a.

Furthermore, as noted above, the flow of irrigating fluid from perforations 60 causes the respective sensed temperatures from at least some of the temperature sensors to be lower, relative to if no irrigating fluid were flowing from perforations 60. To address the above challenges, embodiments of the present invention provide apparatus and methods for estimating the actual temperature of the tissue, at least at the tissue-electrode interface, as described immediately hereinbelow.

Figure 2:
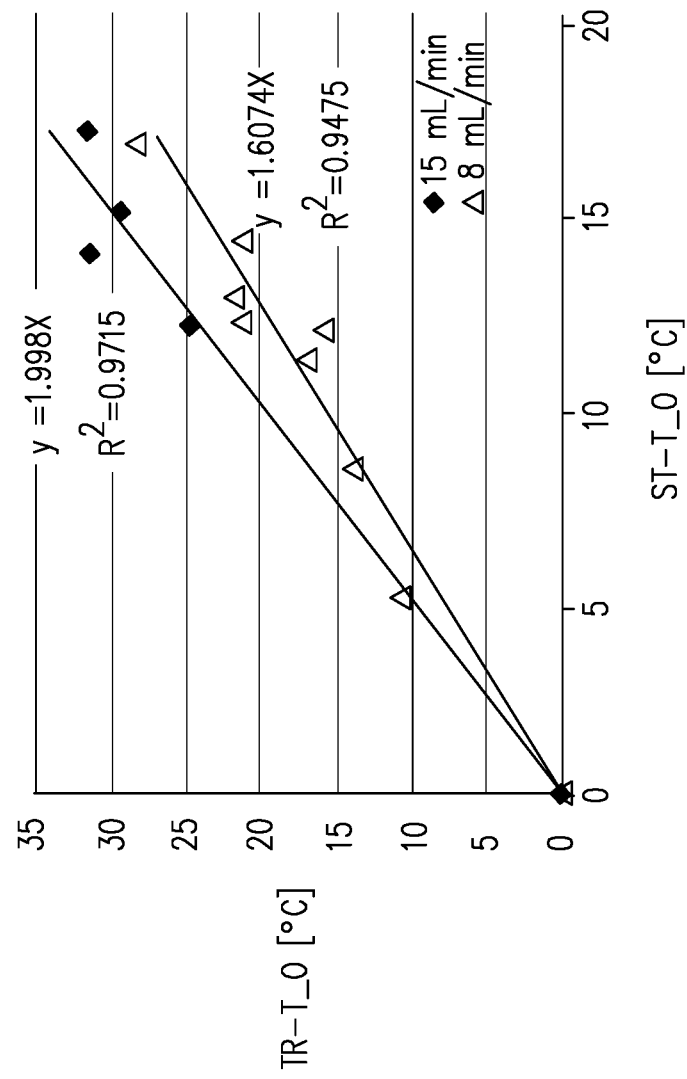
FIG. 2 shows experimental data acquired by the present inventors.

Reference is now made to FIG. 2, which shows experimental data acquired by the present inventors. As further described below, the experimental data of FIG. 2 shows the relationship between the temperature sensed by the temperature sensors and the "actual" measured temperature of the tissue.

To acquire the data, distal end 30 was used to "ablate" ex vivo tissue multiple times. During each of the trial ablations, irrigating fluid was pumped out of the distal end, multiple temperature sensors in the distal end of the catheter were used for sensing, and additionally, a thermometer was used to measure the actual temperature of the tissue at the tissue-electrode interface. Two sets of trial ablations were conducted; a first set with an irrigating-fluid flow rate of 8 mL/min, and a second set with an irrigating-fluid flow rate of 15 mL/min. The trial ablations of each set were conducted with different respective ablation powers, and/or different respective forces of contact between the electrode and the tissue. (Each of these factors affects the temperature at the tissue-electrode interface; for example, increasing the power, and/or increasing the force of contact, increases the temperature.)

Sensed temperature values ST, minus a normalizing temperature T_0 (described below), are plotted along the horizontal axis of FIG. 2. In this particular case, the sensed temperature values ST are the average of the temperatures sensed by the three distal temperature sensors, shown in FIG. 1. The thermometer reading TR, minus T_0, is plotted along the vertical axis. Each point in FIG. 2 thus represents a pair of values (ST-T_0, TR-T_0) for a particular flow rate, ablation power, and force of contact. Typically, a flow rate of 15 mL/min is used only for a relatively high ablation power and/or force of contact; hence, the data for 15 mL/min includes only relatively high temperatures.

As shown in FIG. 2, for each of the flow rates, a linear regression function was fit to the acquired data with a high goodness of fit, as evidenced by the high "R-squared" values. This regression function may be expressed in the form TR-T_0=a(FR)*(ST-T_0), where T_0, ST, and TR are as described above, and a(FR) is a coefficient that is a function of the flow rate of the irrigating fluid. In particular, for a flow rate of 8 mL/min, FIG. 2 shows a coefficient a(FR) of around 1.6, while for a flow rate of 15 mL/min, FIG. 2 shows a coefficient a(FR) of around 2.

T_0 is the value of ST prior to the start of the ablation, e.g., the average temperature sensed over the one second prior to the start of the ablation. Prior to the start of the ablation, TR is typically the same as ST, such that ST=TR=T_0. Hence, the subtraction of T_0 from each of ST and TR, prior to performing the regression, typically simplifies the regression, by causing each of the regressed lines to pass through the origin. Stated differently, the regression is simplified, in that the regression function includes only one variable (i.e., a(FR)), rather than two variables. Notwithstanding the above, it is noted that the regressions depicted in FIG. 2 may be performed even without measuring or using T_0; the measurement and use of T_0 is generally for convenience only.

In any case, the "X" variable in the regression is typically a variable that is based on ST. For example, this variable may be ST itself, or ST-T_0, as described above. Similarly, the "Y" variable in the regression is typically a variable that is based on TR. For example, this variable may be TR itself, or TR-T_0, as described above.

As further described hereinbelow, the regression function illustrated in FIG. 2 may be used to estimate the temperature of the tissue, at least at the tissue-electrode interface, during a live ablation procedure.

As noted above, the trials depicted in FIG. 2 were conducted with TR measured at the electrode-tissue interface. In some cases, during a live procedure, it may be advantageous to estimate the temperature of the tissue at deeper locations within the tissue, e.g., 5 mm beneath the tissue. Hence, the scope of the present invention includes (i) performing ablations (e.g., trial ablations) with TR measured at such deeper locations, thus allowing respective regression functions to be determined for these locations, and (ii) during a live procedure, using the regression functions to estimate the temperature of the tissue at these locations.

In some embodiments, the flow of irrigation fluid roughly affects a subset of, or all of, the temperature sensors in a similar way, such that a(FR) may be learned by averaging the sensed temperatures over the subset of, or all of, the sensors. For example, as noted above, the sensed temperatures shown in FIG. 2 are averages for the three distal sensors, and a single a(FR) is learned for the three distal sensors. In other embodiments, a(FR) may be learned separately for each of one or more of the sensors. FIG. 3A, described immediately hereinbelow, describes such an embodiment.

Reference is now made to FIG. 3A, which is a flow diagram for a method 62 for learning a(FR), in accordance with some embodiments of the present invention. In method 62, a(FR) is learned for one or more flow rates, for each of one or more temperature sensors. For each sensor and flow rate, a(FR) is learned, at a learning step 64, using the technique described above with reference to FIG. 2. In other words, at learning step 64, distal end 30 is used to "ablate" ex vivo tissue using various ablation powers and/or contact forces, while irrigating fluid is pumped out of the distal end. Sensed temperatures and actual temperatures are acquired, and regression (e.g., linear regression) is used to learn a(FR).

In general, since the flow rate of the irrigation fluid may vary over different ablation procedures, and/or may vary during a single ablation procedure, it may be advantageous to learn a(FR) for more than one flow rate. For example, various flow rates within the range of 8-15 mL/min may be of interest, since, during a live procedure, the flow rate is typically between 8 mL/min and 15 mL/min.

For example, a(FR) may first be learned, at learning step 64, for sensor 48a (FIG. 1) and a flow rate of 8 mL/min. Subsequently, at a first decision step 66, a decision is made as to whether to change the current flow rate. If the decision is made to change the current flow rate (e.g., to 15 mL/min), the current flow rate is changed, at a flow-rate-changing step 67. Subsequently, at learning step 64, a(FR) is learned for the second flow rate.

Once a(FR) has been learned for all of the flow rates of interest, method 62 proceeds to a second decision step 68, at which a decision is made as to whether to change the current sensor. If a decision is made to change the current sensor (e.g., to sensor 48b (FIG. 1)), the sensor is changed at a sensor-changing step 69. Subsequently, at learning step 64, a(FR) is learned for the second sensor, for all of the flow rates of interest.

Method 62 ends once a(FR) has been learned for all of the sensors and flow rates of interest.

The inventors have observed that the relationship between the sensed temperature and the measured temperature is often alternatively or additionally dependent on a parameter of the ablating current, such as the power of the ablating current ("ablation power"). Hence, in some embodiments, the learned coefficient "a" is dependent on one or more variables, such as the ablation power, instead of or in addition to the flow rate. Nonetheless, for simplicity, the notation "a(FR)" is used throughout the description, even if the learned coefficient "a" is actually a function of one or more variables instead of or in addition to the flow rate "FR".

Figure 3B:
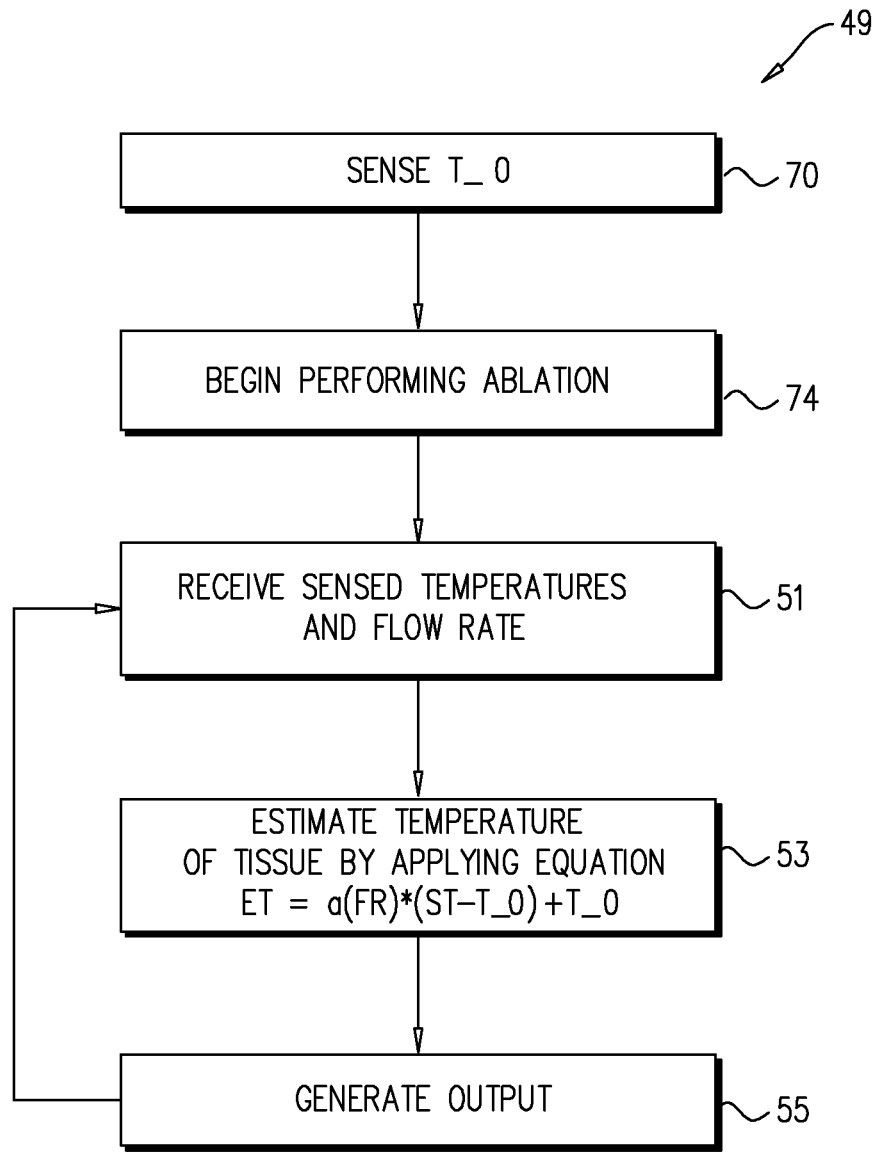
FIG. 3B is a flow diagram for a method for estimating a temperature of tissue, in accordance with some embodiments of the present invention.

Reference is again made to FIG. 1, and is additionally made to FIG. 3B, which is a flow diagram for a method 49 for estimating a temperature of tissue, in accordance with some embodiments of the present invention. Whereas method 62 is typically (but not necessarily) practiced ex vivo and "offline," method 49 is practiced in vivo, during a live ablation procedure.

Method 49 begins with an initial-sensing step 70, at which T_0 is sensed. (Typically, an average over several of the sensors is used for T_0.) Subsequently, at an ablation-beginning step 74, the operating physician begins to perform the ablation. As shown in FIG. 1, system 20 comprises an interface 50 (e.g., a connector and/or port), and a processor 52. Interface 50 is configured to connect to distal end 30 of catheter 22 (e.g., via a wire running through the catheter), and to facilitate communication between the distal end of the catheter and processor 52. Through interface 50, processor 52 receives, at a receiving step 51, the respective temperatures ("ST") sensed by sensors 48 during the ablation procedure. The processor may average these temperatures over a subset of the sensors, or over all of the sensors.

In some embodiments, the processor further receives, at receiving step 51, the fluid-flow rate of the irrigating fluid, e.g., by receiving the fluid-flow rate directly from pump 38. Alternatively or additionally, the processor may receive, at receiving step 51, a parameter of, such as the power of, the ablating current that is output from RF energy generator 34. For example, the processor may receive a signal from the RF generator, or from a measuring device, that indicates the power of the ablating current. In other embodiments, as described below, the processor controls the pump and/or the RF generator, such that the processor generally "knows" the fluid-flow rate and/or the ablating-current parameter even without the performance of receiving step 51.

Subsequently, at an estimation step 53, the processor estimates the temperature of the tissue in the vicinity of electrode 46 (e.g., at the tissue-electrode interface), based at least on (i) one or more of the sensed temperatures (e.g., based on one or more averages of the sensed temperatures), and (ii) the fluid-flow rate of the irrigating fluid and/or the parameter of the ablating current. For example, based on (i) a particular one of the temperatures ST sensed by one of the sensors, and (ii) the corresponding a(FR) value, the processor may compute an estimated temperature ("ET") of the tissue, by applying the equation $ET=a(FR)*(ST-T\_0)+T\_0$. (This equation is equivalent to the regression function described above, with the notation "ET" used in place of "TR.") In other words, the processor selects (i.e., computes, or selects from a lookup table) the appropriate a(FR) for the sensor in response to the flow rate and/or ablating-current parameter, multiplies $ST-T\_0$ by the selected a(FR), and adds $T\_0$, to arrive at the estimated temperature.

In some embodiments, a model is fit to the experimentally-derived values of a(FR). In such embodiments, a coefficient a(FR) that is interpolated from the experimentally-derived coefficients may be selected for the temperature estimation. For example, using linear interpolation, for the values shown in FIG. 2, the selected a(FR) would be approximately 1.7 for a flow rate of 10 mL/min. Alternatively, extrapolation may be used to select a(FR).

Typically, the processor performs a respective estimate for each of the sensed temperatures or averages of the sensed temperatures, and averages the respective estimates to arrive at a "combined" estimate. For example, with reference to FIG. 1, the processor may perform a first estimate for the three distal sensors and a second estimate for the three proximal sensors, and compute the combined estimate by averaging the two separate estimates.

Subsequently, in response to the estimated temperature (e.g., the combined estimate), at an output-generating step 55, the processor generates an output, such as a visual output 57 that indicates the estimated temperature. (Visual output 57 may be shown on a user interface 56, which includes, for example, a touch screen.) In response to the output, operator 28 may adjust the power of the ablating current supplied by RF energy generator 34, e.g., by stopping the ablating current, or by otherwise decreasing the power of the current. Alternatively or additionally, in response to the output, the operator may change the rate of flow of irrigating fluid supplied by pump 38, or change the contact force with which the electrode is pressed against the tissue.

In some embodiments, the operator controls RF energy generator 34 and/or pump 38 via processor 52. In such embodiments, the operator typically provides input to the processor, such as by using user interface 56. In response to the input, the processor generates a control signal 59 that controls the RF energy generator and/or the pump. In other embodiments, processor 52 automatically controls the RF energy generator and/or pump, i.e., the output that is generated in output-generating step 55 includes control signal 59.

Typically, method 49 is repeatedly performed during the ablation procedure, i.e., steps 51, 53, and 55 are repeatedly performed in sequence, such that patient 26 is continually monitored during the procedure.

In general, processor 52 may be embodied as a single processor, or as a cooperatively networked or clustered set of processors. Processor 52 is typically a programmed digital computing device comprising a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. Such program code and/or data, when provided to the processor, produce a machine or special-purpose computer, configured to perform the tasks described herein.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for use with an intra-body probe, a distal end of which includes an ablation electrode and a temperature sensor, the method comprising, using a processor:
   receiving an initial temperature sensed by the temperature sensor before the ablation electrode drives an ablating current into tissue of a subject;
   receiving a temperature sensed by the temperature sensor while the ablation electrode is driving an ablating current into tissue of a subject, and fluid is passed from the distal end of the intra-body probe at a fluid flow rate;
   calculating an estimated temperature of the tissue in the vicinity of the electrode during ablation by adding to the initial sensed temperature, the difference between the sensed temperature during ablation and the initial sensed temperature multiplied by a coefficient selected based on at least one of the fluid flow rate or a parameter of ablating current added to the initial sensed temperature; and
   generating an output in response to the estimated temperature.

2. The method according to claim 1, wherein calculating the estimated temperature of the tissue comprises calculating the estimated temperature of the tissue at an interface of the tissue and the ablation electrode.

3. The method according to claim 1, wherein the temperature is sensed during ablation while the temperature sensor is not in contact with the tissue.

4. The method according to claim 1, further comprising adjusting a power of the ablating current in response to the output.

5. The method according to claim 4, wherein adjusting the power of the ablating current comprises stopping the ablating current.

6. The method according to claim 1, further comprising changing the fluid flow rate, in response to the output.

7. The method according to claim 1, further comprising, in response to the output, changing a force with which the ablation electrode is pressed against the tissue.

8. The method according to claim 1, wherein selecting the coefficient comprises computing the coefficient by interpolation.

9. An apparatus for use with an intra-body probe, a distal end of which includes an ablation electrode and a temperature sensor, the apparatus comprising:
    an interface configured to connect to the intra-body probe; and
    a processor configured to:
        receive an initial temperature sensed by the temperature sensor before the ablation electrode drives an ablating current into tissue of a subject;
        receive a temperature sensed by the temperature sensor while the ablation electrode is driving an ablating current into tissue of a subject, and fluid is passed from the distal end of the intra-body probe at a fluid flow rate,
        calculate an estimated a temperature of the in the vicinity of the electrode during ablation by adding to the initial sensed temperature, the difference between the sensed temperature during ablation and the initial sensed temperature multiplied by a coefficient selected based on at least one of the fluid flow rate or a parameter of ablating current added to the initial sensed temperature; and
        generate an output in response to the estimated temperature.

10. The apparatus according to claim 9, wherein the processor is configured to calculate the estimated temperature of the tissue at an interface of the tissue and the ablation electrode.

11. The apparatus according to claim 9, wherein the processor is configured to, by generating the output, adjust a power of the ablating current.

12. The apparatus according to claim 11, wherein the processor is configured to, by generating the output, stop the ablating current.

13. The apparatus according to claim 9, wherein the processor is configured to, by generating the output, change the fluid-flow rate.

* * * * *